United States Patent
Lee

(10) Patent No.: US 8,962,004 B2
(45) Date of Patent: Feb. 24, 2015

(54) ENCAPSULATED TRIAZINYL SULFONYLUREA HERBICIDE AND METHODS OF USE

(75) Inventor: James C. Lee, Valdosta, GA (US)

(73) Assignee: Arysta Lifescience North America, LLC, Cary, NC (US)

( * ) Notice: Subject to any disclaimer, the term of this patent is extended or adjusted under 35 U.S.C. 154(b) by 0 days.

(21) Appl. No.: 13/440,652

(22) Filed: Apr. 5, 2012

(65) Prior Publication Data

US 2012/0309621 A1    Dec. 6, 2012

Related U.S. Application Data

(60) Provisional application No. 61/497,433, filed on Jun. 15, 2011, provisional application No. 61/472,062, filed on Apr. 5, 2011.

(51) Int. Cl.
| | | |
|---|---|---|
| A01N 25/34 | (2006.01) | |
| A61K 9/48 | (2006.01) | |
| A01N 43/46 | (2006.01) | |
| A01N 43/707 | (2006.01) | |
| A01N 25/28 | (2006.01) | |

(52) U.S. Cl.
CPC ..................... *A01N 25/28* (2013.01)
USPC ........... 424/408; 424/451; 424/463; 504/227; 504/229

(58) Field of Classification Search
None
See application file for complete search history.

(56) References Cited

U.S. PATENT DOCUMENTS

| | | | | |
|---|---|---|---|---|
| 5,597,780 | A * | 1/1997 | Lee et al. ........................ | 504/271 |
| 6,566,306 | B1 * | 5/2003 | Wolf et al. ...................... | 504/127 |
| 2004/0048749 | A1 * | 3/2004 | Zerrer et al. ................... | 504/359 |
| 2010/0130364 | A1 * | 5/2010 | Casana Giner et al. ........ | 504/133 |

* cited by examiner

*Primary Examiner* — Alton Pryor
(74) *Attorney, Agent, or Firm* — Pillsbury Winthrop Shaw Pittman LLP

(57) ABSTRACT

The invention relates to compositions including an encapsulated triazinyl sulfonylurea. The invention further relates to methods for controlling weeds. The invention additionally provides methods for producing such compositions.

82 Claims, No Drawings

ENCAPSULATED TRIAZINYL SULFONYLUREA HERBICIDE AND METHODS OF USE

RELATED APPLICATIONS

This application claims the benefit of priority of application Ser. No. 61/497,433, filed Jun. 15, 2011, and application Ser. No. 61/472,062, filed Apr. 5, 2011, all of which applications are expressly incorporated herein by reference in their entirety.

FIELD OF THE INVENTION

The disclosure relates to a stable composition including an encapsulated triazinyl sulfonylurea, which can be used for controlling weeds.

INTRODUCTION

Triazinyl sulfonylureas are widely used in agriculture. In general, triazinyl sulfonylureas are stable to neutral to alkaline solutions (i.e. pH 7 and above), but are hydrolyzed under acidic conditions. In moist field soils, triazinyl sulfonylureas may degrade via the cleavage of the sulfonylurea linkage if the soil is acidic. For example, tribenuron methyl hydrolyzes rapidly under acidic conditions at 25° C., but is stable under alkaline conditions [$DT_{50}$<24 hours, 3-16 days, and >>30 days at pH 5, 7, and 9, respectively] (Venzon, 1985).[1] Therefore, the persistence of triazinyl sulfonylureas is much lower at low soil pH. Thus, there exists a need to protect triazinyl sulfonylureas from degradation in acidic environment.

[1] Venzon, E M (1985) Hydrolysis of [$^{14}$C-Phenyl] and [14C-Tnazme]DPX-L5300m, DuPont Internal Report, AMR 385-85; source: Roberts, Hutson; Metabolic pathways of agrochemicals, part 2, p.571.

Compositions containing one or more herbicides are desirable in agricultural for broadening the spectrum or range of unwanted weed and plant species killed or controlled. Applying combinations of herbicidal compounds may also enhance the herbicidal effectiveness. Compositions containing combinations of herbicide with one or more insecticide and/or fungicide are also desirable in agricultural for controlling both unwanted vegetation and insects and/or fungi.

SUMMARY OF THE INVENTION

The invention provides among other things stable compositions including a triazinyl sulfonylurea encapsulated with a silicone defoaming agent. In certain embodiments, examples of triazinyl sulfonylurea include tribenuron methyl, triflusulfuron methyl, metsulfuron methyl, iodosulfuron, cinosulfuron, prosulfuron, triasulfuron, tritosulfuron, chlorsulfuron, thifensulfuron methyl and ethametsulfuron-methyl. In one embodiment, a triazinyl sulfonylurea is tribenuron methyl.

A silicone defoaming agent can be polydimethylsiloxane. In one embodiment, a polydimethylsiloxane has a viscosity of from 10 cSt to 100,000 cSt. In another embodiment, a polydimethylsiloxane is present in an amount of from 0.01% to 5%, or from 0.05% to 1% by weight of the total weight of the composition.

A stable herbicidal compositions may further include a silica, which can be a hydrophobic or a hydrophilic silica. A silica can be a fumed or precipitated. In one embodiment, a silica is present in an amount of from 0.01% to 5% or from 0.05% to 1% by weight of the total weight of the composition. In another embodiment, the weight ratio of the triazinyl sulfonylurea to the silicone defoaming agent is from 30 to 0.5. In yet another embodiment, the weight ratio of the silicone defoaming agent to the silica is from 10 to 0.1.

The invention provides compositions further including one or more active compounds. In certain embodiments, the active compound is a herbicide. In one embodiment, the herbicide includes an aryloxyalkanoic acid. In certain embodiments, examples of aryloxyalkanoic acids include fluoroxypyr meptyl, 4-CPA, 2,4-D, MCPA, Mecoprop, Mecoprop-P, 2,4,5-T, 3,4-DB, MCPB, 2,4,5-TB, cloprop, 4-CPP, dichorprop, dichlorprop-P, fenoprop, and Triclopyr. In one particular embodiment, the aryloxyalkanoic acid is fluoroxypyr meptyl. An aryloxyalkanoic acid can be present in an amount of from 10% to 75% or from 20% to 50% by weight of the total weight of the composition. In certain embodiments, the herbicide further includes an additional triazinyl sulfonylurea. In one embodiment, the additional triazinyl sulfonylurea is thifensulfuron methyl. An additional triazinyl sulfonylurea can be present in an amount of from 1% to 10% by weight of the total weight of the composition.

The invention provides compositions contain no more than about 3% by weight of moisture. In one embodiment, a composition has a pH of at least 8.0. In a further embodiment, a composition has a pH between 9.0 to 10.0.

In certain embodiments, the invention provides compositions including i) tribenuron methyl encapsulated with polydimethylsiloxane and a hydrophilic silica, ii) fluoroxypyr meptyl, and iii) thifensulfuron methyl. In one embodiment, composition includes from 1% to 2% by weight of tribenuron methyl based on the total weight of the composition. In one embodiment, composition includes from 35% to 40% by weight of fluoroxypyr meptyl based on the total weight of the composition. In one embodiment, composition includes from 3% to 6% by weight of thifensulfuron methyl based on the total weight of the composition. In one embodiment, composition includes from 0.01% to 5% by weight of polydimethylsiloxane based on the total weight of the composition. In one embodiment, composition includes from 0.05% to 1%, or from 0.1% to 0.8% by weight of silica based on the total weight of the composition.

The invention also provides methods of controlling weeds. In one embodiment, a method includes contacting the weed with a composition of the invention in an amount effective inhibit growth of the weed. In particular embodiments, a method includes applying a composition including an encapsulated triazinyl sulfonylurea selected from the group consisting of tribenuron methyl, metsulfuron methyl, ethametsulfuron methyl, cinosulfuron, prosulfuron, triasulfuron, tritosulfuron, chlorsulfuron, and ethametsulfuron-methyl. In one embodiment, a method includes applying a composition including tribenuron methyl.

Methods of the invention include control of a weed. In certain embodiments, the weed is selected from the group consisting of annual knawel, annual sowthistle, black mustard, bushy wallflower/treacle mustard, broadleaf dock, but buttercup, canada thistle, carolina geranium, catchweed bedstraw (cleavers), coast fiddleneck, coffee weed, common chickweed, common cocklebur, common groundsel, common lambsquarters, common purslane, common ragweed, common sunflower, common tarweed, corn chamomile, corn spurry, cow cockle, cress (mouse ear), curly dock, devilsclaw, false chamomile, field bindweed, field horsetail, filaree (Texas redstem), flixweed, giant ragweed, grape species, green smartweed, horseweed, hedge bindweed, hemp dogbane, henbit, jimsonweed, knotweed, kochia, ladysthumb, lanceleaf sage, london rocket, common mallow, little mallow, venice mallow, marestail, marshelder, miners lettuce, morningglory, mouseear chickweed, narrowleaf lambsquarters, nightflowering catchfly, nightshade species, pennsylvania smartweed, pepperweed species, pineappleweed, prickly lettuce, prostrate knotweed, prostrate pigweed, puncturevine, redmaids, redroot pigweed, russian thistle, scentless chamomile/mayweed, shepherd's purse, slimleaf lambsquarters, smallflower lentils, volunteer peas, volunteer sunflower, wild buckwheat, wild chamomile, wild garlic, wild mustard, wild radish, charlock, deadnettle red, fat hen, forget-me-not, fumitory, hemp-nettle common, poppy common, redshank, shepherds purse, cranesbill, bindweed black, knotgrass, marigold corn, orache, pansy, poppy, speedwell common field, speedwell wall, buttercup, docks, speedwell ivy-leaved, volunteer beans, and volunteer OSR.

A composition can be applied as a post-emergence or pre-emergence treatment. In one embodiment, a composition is applied to a crop plant in need of weed control or at risk of undesirable weeds. Such a crop plan can be, for example, any of wheat, barley, oat, triticale, cereals, rice, maize, sorghum, sugar cane, cotton, canola, turf, barley, pinapple, potato, sweet potato, sunflower, rye, corn, soybean, sugar beet, tobacco, safflower, tomato, alfalfa and cassava.

The invention also provides methods for producing an encapsulated triazinyl sulfonylurea composition, including: a) mixing a triazinyl sulfonylurea with a silicone defoaming agent to form an encapsulated triazinyl sulfonylurea mixture; and b) drying the resulting mixture obtained from step a) to remove moisture, thereby forming the encapsulated triazinyl sulfonylurea composition. In a further embodiment, a method further includes adding one or more active or inactive compounds to the encapsulated triazinyl sulfonylurea mixture of step a) to form a second mixture. In one embodiment, a method further includes adding fluoroxypyr to the encapsulated triazinyl sulfonylurea mixture of step a) to form a second mixture. In one embodiment, a method further includes adding thifensulfuron-methyl to the encapsulated triazinyl sulfonylurea mixture of step a) to form a second mixture. In a further embodiment, a method further includes adding one or more adjuvant to the encapsulated triazinyl sulfonylurea mixture of step a) to form a second mixture. In yet a further embodiment, a method further includes in step a) further comprises mixing the triazinyl sulfonylurea with a silica. In one embodiment, a method for producing an encapsulated triazinyl sulfonylurea composition, including mixing a triazinyl sulfonylurea with a silicone defoaming agent comprises a polydimethylsiloxane.

DETAILED DESCRIPTION OF THE INVENTION

The invention is based in part on the encapsulation of a triazinyl sulfonylurea with a silicone defoaming agent. Such encapsulation can greatly increase the stability of triazinyl sulfonylurea in a composition, including, for example, combinations with other actives and inactives. The invention therefore provides such compositions and methods of making and using such compositions for weed control.

The terms "encapsulated" or "encapsulation" as used herein refers to admixing an active compound, such as triazinyl sulfonylurea, with a silicone defoaming agent(s) which forms a barrier or coating of the silicone defoaming agent onto the triazinyl sulfonylurea. The active compound may be fully or partially encapsulated by the silicone defoaming agent(s).

Non-limiting examples of triazinyl sulfonylurea include methyl 2-[4-methoxy-6-methyl-1,3,5-triazin-2-yl(methyl) carbamoylsulfamoyl]benzoate (tribenuron methyl), 1-[(2 methoxycarbonylphenyl)-sulfonyl]-3-(4-methoxy-6-methyl-1,3,5-triazin yl-2-yl)urea (metsulfuron-methyl), 1-(4,6-dimethoxy-1,3,5-triazin-2-yl)-3-[2-(2-methoxyethoxy)phenylsulfonyl]urea (cinosulfuron), 1-(4-methoxy-6-methyl-1,3,5-triazin-2-yl)-3-[2-(3,3,3-trifluoropropyl)phenylsulfonyl]urea (prosulfuron), 1-[2-(2-chloroethoxy)phenylsulfonyl]-3-(4-methoxy-6-methyl-1,3,5-triazin-2-yl)urea (triasulfuron), 1-[4-methoxy-6-(trifluoromethyl)-1,3,5-triazin-2-yl]-3-[2-(trifluoromethyl)benzenesulfonyl]urea (tritosulfuron), 1-(2-chlorophenylsulfonyl)-3-(4-methoxy-6-methyl-1,3,5-triazin-2-yl)urea (chlorsulfuron), methyl 3-(4-methoxy-6-methyl-1,3,5-triazin-2-ylcarbamoylsulfamoyl)thiophene-2-carboxylate (thifensulfuron methyl), and methyl 2-[(4-ethoxy-6-methylamino-1,3,5-triazin-2-yl) carbamoylsulfamoyl]benzoate (ethametsulfuron-methyl), 2-[4-dimethylamino-6-(2,2,2-trifluoroethoxy)-1,3,5-triazin-2-ylcarbamoylsulfamoyl]-m-toluic acid (triflusulfuron), and 4-iodo-2-[(4-methoxy-6-methyl-1,3,5-triazin-2-yl)carbamoylsulfamoyl]benzoic acid (iodosulfuron).

Certain triazinyl sulfonylureas are acid labile, for example, tribenuron methyl. A triazinyl sulfonylurea may have a half life of more than 5 days at an alkaline environment, or a pH of greater than 8. Accordingly, the invention compositions and methods include stabilizing or stabilized forms of triazinyl sulfonylurea, including tribenuron methyl.

The concentration of triazinyl sulfonylurea in the composition can vary. In certain embodiments, the percentage by weight (weight percent) of a triazinyl sulfonylurea in the composition is between 0.05% and 20%. In other embodiments, the percentage by weight of a triazinyl sulfonylurea in the composition is between 0.05% and 10%, 0.5% and 5%, or between 1% and 2%.

The terms "antifoam agent," "defoaming agent," and "defoamer" are used interchangeably herein. A "silicone deforming agent" has an Si group and can include multiple Si groups as in a polymer. Silicone defoaming agents can be used for their surface tension lowering characteristics or to inhibit the formation of bubbles in a liquid during its agitation. In this invention, silicone defoaming agents can be used to inhibit, reduce or prevent absorption of moisture due to the hydrophobic properties of silicone.

Silicone defoaming agents for encapsulation of triazinyl sulfonylurea include polysiloxanes. One non-limiting example of such a polysiloxane is polydimethylsiloxane.

In certain embodiments, a polydimethylsiloxane has a viscosity of at least 0.5 cSt (mm2/s), from 10 cSt to 100,000 cSt, from 50 cSt to 60,000 cSt, from 500 cSt to 8000 cSt, or from 1000 cSt to 5000 cSt. A silicone defoaming agent can be present in a composition in an amount of from 0.01% to 5% by weight of the total weight of the composition, and particularly from 0.05% to 1% by weight of the total weight of the composition. Typically, the amount of a silicone defoaming agent, (e.g., by weight) will be less than the amount of a triazinyl sulfonylurea. The weight ratio of a triazinyl sulfonylurea to a silicone defoaming agent can be from 30 to 0.5, from 20 to 1, from 15 to 1, or from 10 to 2.5. A silicone defoaming agent, in particular, a polydimethylsioxane, may further include a silica. For example, some of the commercially available polydimethylsiloxanes are silica-filled polydimethylsiloxanes (PDMS).

Suitable Silicone defoaming agents are available from DOW CORNING (Dow Corning Corporate Center, Midland, Mich., U.S.A.) which include: DOW CORNING 200 Fluids (e.g. 500 cSt), Antifoam 1400 and 2-3436 antifoam. Silicone defoaming agents suitable are also available from Wacker-Chemie AG, Germany, which include: WACKER AK 1 000 silicone fluid, and from Momentive Performance Materials, Columbus, Ohio, U.S.A., which include: SAG 47 and SAG 1538.

In certain embodiments, a composition and method of the invention can include silica. In a particular embodiment, triazinyl sulfonylurea is encapsulated with a silicone defoaming agent and one or more silicas. Similar to the functions of the silicone defoaming agents in this invention, silica can be used to inhibit, reduce or prevent absorption of moisture in the compositions. Thus, a triazinyl sulfonylurea can be coated with a silicone defoaming agent, such as a polydimethylsioxane, and a silica, such as a hydrophobic silica, a hydrophilic silica or a mixture thereof.

A silica may be pyrogenic (fumed) or precipitated. A silica can have a BET (Brunauer-Emmett-Teller) surface area of from 10 to 1000 m$^2$/g, or 10 to 400 m$^2$/g.

The pH value of a silica is not limited, but may be slightly alkaline. For example, the pH value of a silica may be in the range between 7.0 to 11.0, or in the ranges between 8.5 to 10.5, between 7.5 to 10, or between 7.8 to 9.4.

The amount of silica present in the composition is not limited, but is typically is from 0.01% to 5%, or from 0.05% to 1% by weight of the total weight of the composition. The weight ratio of a triazinyl sulfonylurea to a silica can be from 50:1 to 1:50. The weight ratio of a silicone defoaming agent to a silica can be from 100:1 to 1:100, from 10:1 to 1:10, or from 10:1 to 1:2, or from 2:1 to 1:1.

In one embodiment, a silica for encapsulation of a triazinyl sulfonylurea with a silicone defoming agent may be different than the silica present in a silicone defoaming agent. For example, certain commercially available polydimethylsiloxanes contain silica (i.e. silica-filled polydimethylsiloxanes), where such silica is different from the silica used for encapsulation of a triazinyl sulfonylurea with a silicone defoming agent.

Commercially available hydrophilic silicas useful in accordance with the invention include Sipernat® D17, a precipitated silica having a BET surface area of about 100 m$^2$/g (available commercially under the name from Evonik Degussa, Germany); Aerosil R-504, a fumed silica treated with HMDS and aminosilane having a BET surface area of about 150 m$^2$/g (available commercially under the name from Evonik Degussa, Germany); Sipernat® 35, a precipitated and slightly alkaline silica having a BET surface area of about 170 m$^2$/g; Sipernat® 350, a precipitated and slightly alkaline silica having a BET surface area of about 50 m$^2$/g.

In certain embodiments, the invention provides methods and compositions including an encapsulated triazinyl sulfonylurea and one or more non-encapsulated or encapsulated active or inactive (inert) compound(s). These additional compounds, include herbicides, fungicides, insecticides, acaricides, nematicides, bird repellents, growth substances, plant nutrients and agents which improve soil structure. Compositions of the invention may affirmatively exclude any of the aforementioned actives or inactives.

For a non-encapsulated active compound, the percentage by weight of a non-encapsulated active compound within in a composition is between 0.05% and 90%, between 0.5% and 80%, between 0.1% and 20%, between 0.5% and 10%, between 1% and 10%, between 2% and 8%, between 3% and 6%, between 4% and 5%, between 10% and 75%, between 15% and 60%, between 20% and 50%, between 30% and 45%, between 35% and 40%, or between 35% and 37%.

As disclosed herein, any active or inactive compound may be combined with an encapsulated triazinyl sulfonylurea in a composition according to the invention. Non-limiting specific examples of active compounds useful in combination with a triazinyl sulfonylurea according to the invention include: acetanilides, amides, amidines, anilides, arylaminopropionic acids, arylalanines, aryloxycarboxylic acids, aryloxyplenoxy-propionates ("fops"), azoryls, benzilates, benzofurans, benzoic acids, benzoylcyclohexanediones, benzofuranyl alkylsulfonates, benzothiazoles, benzoxazoles, benzoylpyrazoles, bipyridyliums, carbamates, carbanilates, carboxamides, chloroacetamides, chloroacetanilides, chlorotriazines, cyclodienes, cyclohexanediones ("dims"), cyclohexane oximes, cyclopropylisoxazoles, dicarboximides, dinitroalilines, dinitrophenols, diphenyl ethers, dithiocarbamates, dithiolanes, glycines, halogenated aliphatics, imidazoles, imidazolinones, isoazolidinones, methoxytriazines, methylthiotriazines, neonicotinoids, nitriles, nitroanilines, nitrophenylethers, N-phenylphthalimides, organoarsenicals, organophosphates, organophosphorus, oxadiazines, oxadiazolinones, oxazoles, oxyacetamides, phenoxyalkanoic acids, phenyl carbamates, ureas, phenoxys (including substituted phenoxys), phenoxyacetics, phenoxybutyrics, phenoxycarboxylic acids, phenoxypropionics, phenylamides, phenylethylenediamines, phenylpyrazoles, phenylpyridazines, phenylureas, phosphinic acids, phosphorodithioates, phthalic acids, picolinic acids, pyrazoles, pyrethroids, pyridazines, pyridazinones, pyridines, pyridine carboxylic acids, pyrimidinamines, pyrimidinyloxybenzoic acids, pyrimidinylthiobenzoic acids, quaternary ammoniums, quinazolinones, quinoline carboxylic acids, strobilurins, sulfonamides, sulfonanilides, sulfonylaminocarbonyltriazolinones, sulfonylureas, tetrazolinones, thiadiazoles, thiadiazolylureas, thiocarbamates, thiocarbonates, thioureas, triazines, triazoles, triazolones, triazinones, triazolopyrimidines, triketones, uracils, and ureas (including substituted ureas).

In certain embodiments, the invention provides methods and compositions including an encapsulated triazinyl sulfonylurea and a non-encapsulated active or inactive compound. In one embodiment, a non-encapsulated active compound is a sulfonylurea. One particular example of sulfonylurea is 4,5-dihydro-3-methoxy-4-methyl-5-oxo-N-[2-(trifluoromethoxy)phenylsulfonyl]-1H-1,2,4-triazole-1-carboxamide (flucarbazone). Another particular example of sulfonylurea is 1-(4,6-dimethoxypyrimidin-2-yl)-3-(2-ethylsulfonylimidazo[1,2-a]pyridin-3-ylsulfonyl)urea (sulfosulfuron). In another embodiment, a non-encapsulated active compound is a triazinyl sulfonylurea. A non-encapsulated triazinyl sulfonylurea may include any triazinyl sulfonylurea herbicide disclosed herein. In particular, a non-encapsulated a triazinyl sulfonylurea includes 2-[4-methoxy-6-methyl-1,3,5-triazin-2-yl(methyl)carbamoylsulfamoyl]benzoic acid (tribenuron), 2-(4-methoxy-6-methyl-1,3,5-triazin-2-ylcarbamoylsulfamoyl)benzoic acid (metsulfuron), 1-(2-chlorophenylsulfonyl)-3-(4-methoxy-6-methyl-1,3,5-triazin-2-yl)urea (chlorsulfuron), and 4,5-dihydro-3-methoxy-4-methyl-5-oxo-N-[2-(trifluoromethoxy)phenylsulfonyl]-1H-1,2,4-triazole-1-carboxamide (flucarbazone). In one embodiment, a non-encapsulated triazinyl sulfonylurea is methyl 3-(4-methoxy-6-methyl-1,3,5-triazin-2-ylcarbamoylsulfamoyl)thiophene-2-carboxylate (thifensulfuron methyl).

In certain embodiments, a non-encapsulated active compound includes an aryloxyalkanoic acid. Non-limiting examples of aryloxyalkanoic acid useful according to the invention include fluoroxypyr meptyl, 4-chlorophenoxyacetic acid (4-CPA), (2,4-dichlorophenoxy)acetic acid (2,4-D), 4-chloro-o-tolyloxyacetic acid (MCPA), (RS)-2-(4-chloro-o-tolyloxy)propionic acid (Mecoprop), (R)-2-(4-chloro-o-tolyloxy)propionic acid (Mecoprop-P), (2,4,5-trichlorophenoxy) acetic acid (2,4,5-T), 4-(3,4-dichlorophenoxy)butyric acid (3,4-DB), 4-(4-chloro-o-tolyloxy)butyric acid (MCPB), 4-(2, 4,5-trichlorophenoxy)butyric acid (2,4,5-TB), (RS)-2-(3-chlorophenoxy)propionic acid (cloprop), (RS)-2-(4-chlorophenoxy)propionic acid (4-CPP), (2RS)-2-(2,4-dichlorophenoxy)propionic acid (dichorprop), (2R)-2-(2,4-dichlorophenoxy)propionic acid (dichlorprop-P), (RS)-2-(2,4,5-trichlorophenoxy)propionic acid (fenoprop), and 3,5,6-trichloro-2-pyridyloxyacetic acid (triclopyr). In a particular aspect, a non-limiting example is aryloxyalkanoic acid such as 1-methylheptyl 2-[(4-amino-3,5-dichloro-6-fluoro-2-pyridinyl)oxy]acetate (fluoroxypyr meptyl).

In certain embodiments, a non-encapsulated active compound is an active or inactive compound stable in acidic media (e.g. pH<7.0).

In certain embodiments, the non-encapsulated active compound is a low melting active or inactive compound. Low melting active compounds according to the invention includes compounds having a melting point of less than about 100° C., or less than about 90° C., or less than about 85° C., or less than about 80° C., or less than about 75° C., or less than about 70° C. In certain embodiments, a low melting compound has a melting point in the range of about 20° C. to about 100° C. In specific embodiments, a low melting compound has a melting point in the range of about 30° C. to about 100° C., about 30° C. to about 90° C., about 30° C. to about 80° C., about 30° C. to about 70° C., about 40° C. to about 90° C., about 40° C. to about 80° C., about 40° C. to about 90° C., about 50° C. to about 80° C., or about 50° C. to about 70° C.

In certain embodiments, methods and compositions of the invention includes i) an encapsulated tribenuron methyl, ii) a non-encapsulated fluoroxypyr meptyl, and iii) a non-encapsulated thifensulfuron methyl.

In certain embodiments, a method or composition of the invention include i) tribenuron methyl encapsulated with polydimethylsiloxane and a hydrophilic silica, ii) fluoroxypyr meptyl, and iii) thifensulfuron methyl.

Compositions and methods of the invention can include one or more compound(s) useful for establishing or maintaining pH within a specified range. The pH of the composition can be above 7.0, for example, where the pH of the composition is above 8.0. Typically, the pH of the composition is between about 8.0 and about 12.0, or between about 8.0 to about 10.0, or between about 9.0 to about 10.0. In various embodiments, the composition may include any material capable of adjusting or providing a desired pH, such as a pH that is generally alkaline. This can typically be accomplished through incorporation of an organic or inorganic base. Non-limiting particular examples of compounds useful as pH adjusters include a weak base, for example, sodium carbonate (monohydrate), sodium bicarbonate, or potassium carbonate.

The amount of the pH adjuster included can vary depending upon the desired effect. In certain embodiments, the amount of the pH adjuster can be based upon the desired pH of the composition. For example, the content of the pH adjuster can be an amount sufficient to maintain the pH of the composition greater than or equal to 7.0, at a pH of about 7.0 to about 12.0 or about 8.0 to about 10.0. For example, in other embodiments, the amount of a pH adjuster in the composition is from about 0.1% to about 10% by weight of the composition. More particularly, from about 0.1% to about 5%, or from about 0.5% to about 3%, or from about 1% to about 2% by weight of the composition.

Compositions and methods of the invention can further comprise one or more adjuvant(s). Non-limiting adjuvants include, for example, diluent, wetting agent, dispersant, binder, carrier, surfactant, or any other compound compatible or useful in herbicidal compositions.

Compositions and methods can also include one or more diluents that extend or increase the volume of the composition. Any solid or liquid compound typically recognized as useful as a diluent can be used according to the invention. The diluent is formed of a material that is also useful for facilitating the formation of a solid form of the composition. In particular embodiments, a diluent is chosen based on certain physical characteristics, such as pH and particle size distribution. For example, a diluent can include a material having a pH sufficiently close to the desired formulation pH, as more fully described herein, to avoid the need for excess pH adjusting compound.

Non-limiting examples of materials useful as diluents according to the invention include diatomaceous earth, fine silica, clay, kaolin, feldspar, talc, glass, quartz, wood flour, synthetic fertilizers, dried and pulverized biological sludge and the like. Many suitable solid diluents from the herbicide or insecticide art can be used, e.g., as described by Watkins et al in "Handbook of Insecticide Dust Diluents and Carriers," Caldwell, N.J. Typical liquid diluents and solvents are described in Marsden, "Solvents Guide," 2nd Edition, Interscience, New York, 1950.

In certain embodiments, a diluent may be a silica. For example, Sipernat 35 may be used as a diluent in the compositions. Silica can be added to compositions of the invention to improve the flowable properties in the milling process and to facilitate disintegration of the granules. For example, Sipernat® 350 can be used as a free flow agent.

The content of diluent in the composition can vary depending upon a desired overall composition. In certain embodiments, diluent content in the composition is less than 50% by weight of the composition. In further embodiments, diluent content can be about 0.01% by weight to about 20% by weight, about 0.05% by weight to about 10% by weight, about 0.05% by weight to about 5% by weight, about 0.05% by weight to about 1% by weight, or about 20% by weight to about 60% by weight. In particular embodiments, the amount of diluent present in the formulation is 100% minus the sum of the weight percent of all other formulation components.

The composition may include one or more surfactants. In general, surfactants include dispersing agents, wetting agents and the like. Surfactants useful for formulating compositions are subject to no specific limitation. For example, any of cationic surfactants, nonionic surfactants, anionic surfactants, amphoteric surfactants, phosphate ester surfactant, silicone surfactants may be used.

A surfactant may be present in any desired amount. For example, any one surfactant may be present in an amount of from 0.1% to 50%, from 0.1% to 1%, from 1% to 5%, from 5% to 10%, from 10% to 20%, from 20% to 30%, or 30% or (e.g. 40% or more) more by weight of the composition.

Non-limiting examples of suitable nonionic surfactants include alkylpolyglucosides; glycerol esters such as glyceryl monolaurate, and ethyoxylated glyceryl monococoate; ethoxylated castor oil; ethoxylated reduced sugar esters such as polyoxyethylene sorbitol monolaurate; esters of other polyhydric alcohols such as sorbitan monolaurate and sucrose monostearate; alcohol ethoxylates such as fatty alcohol ethoxylates (e.g., oleyl alcohol ethoxylate), tridecylalcohol ethoxylates and other alcohol ethoxylates such as NEODOL® and oxoalcohol ethoxylates; and ethylene oxide/propylene oxide copolymers such as PLURONIC® type, TETRONIC® type, or TERGITOL XH® type.

Non-limiting examples of suitable anionic surfactants include fatty soaps such as ammonium tallowate and sodium stearate; alkyl sulfates such as sodium $C_{8-10}$ alcohol sulfate, sodium oleyl sulfate, and sodium lauryl sulfate; sulfated oils such as sulfated castor oil; ether sulfates such as sodium lauryl ether sulfate, ammonium lauryl ether sulfate, and ammonium nonylphenol ether sulfate; sulfonates such as petroleum sulfonates, alkylbenzene sulfonates (e.g., sodium (linear) dodecylbenzene sulfonate or sodium (branched) dodecylbenzene sulfonate), alkylnapthalene sulfonates (e.g., AGNIQUE ANS 3DNPW manufactured by Cognis Corporation, which is a mixture of alkylnapthalene sulfonate and dioctyl sulfosuccinate sodium salt.), alkyl sulfonates (e.g., alpha olefin sulfonates), lignosulfonates (e.g. STEPSPERSE® DF-200 and STEPSPERSE® DF-500 manufactured by Stepan Company), sulfosuccinates such as dialkylsulfosuccinates (e.g., sodium dioctylsulfosuccinate) and monoalkylsulfosuccinate and succinamides (e.g., disodium laurylsulfosuccinate and disodium N-alkylsulfosuccinamate); sulfonated amides such as sodium N-methyl N-coco taurate; isethionates such as sodium cocoyl isethionate; sarcosinates such as N-lauroyl sarcosine.

Non-limiting examples of suitable silicone surfactants include ethoxylated or propoxylated silicone based surfactants, e.g., SILLOUETTE® L-77 or BREAK-THRU® S-200.

Non-limiting examples of suitable polymeric surfactants include modified or unmodified styrene acrylic polymer, such as Atlox Metasperse™ 550S manufactured by Croda International Plc. Modified or unmodified styrene acrylic polymers are particularly useful as a dispersant. Other polymer surfactant examples include Agrilan 755 (a hydrophilic comb polymer) manufactured by Akzo Nobel Surface Chemistry LLC Chemtrec, Chicago, Ill., U.S.A.

Other suitable non-limiting dispersants include Supragil MNS 90, Supragil MNS-425 (from Rhodia), Borresperse NA, Borresperse 3A (Lingo Tech.) Tersperse 2100, Tersperse 2425 (Huntsman), Agnique NSC 2NP-U, Agnique NSC 4WNP, Agnique NSC 11NP (Cognis, It is BASF now), Morwet D-425, Morwet D-809, Morwet D-390 (Akzo), Rhodacal BX-78. (Rhodia), REAX 45A, 83A, 85A, and 100M, POLYFON H, O, T, and F (Meadwestvaco).

Other suitable non-limiting wetting agents include Supragil WP, Supragil NK (from Rhodia), Agnique ANS 3DNPW, Agnique ANS 4DNP, Agnique 3DNP-U (Cognis, it is BASF now), Morwet EFW, Morwet B, Morwet IP (Akzo), Aerosol OT-B (Dioctyl sodium sulfosuccinate) (from Cytec), Dispersogen HR(Clariant).

The compositions and methods may include one or more binders. A binder may be in an amount of from 5% to 80% by weight in the composition. In further embodiments, a binder may be in an amount of from 10% to 50%, or from 15% to 30% by weight in the composition. Binders useful in the invention are subject to no specific limitation. For example, lactose, starch, hydrogenated starch, hydrolysate, dextrin, cellulose, methyl cellulose, ethyl cellulose, carboxymethyl cellulose, hydroxyethyl cellulose, hydroxypropyl cellulose, carboxymethyl starch, pullulan, sodium alginate, ammonium alginate, alginic acid propylene glycol ester, guar gum, locust bean gum, xanthane gum, gelatine, casein, polyvinyl alcohol, polyethylene oxide, polyethylene glycol, ethylene/propylene block polymer, sodium polyacrylate, polyvinylpyrrolidone and the like.

The compositions may include one or more carriers. A carrier may be present in an amount of from 1% to 30% by weight in the composition. In further embodiments, a binder may be present in an amount of from 3% to 20%, or from 5% to 10% by weight in the composition. Carriers useful for formulating compositions of the invention are subject to no specific limitation. Examples of inorganic carriers including clay (e.g. Paragon Clay manufactured by Kentucky Tennessee Clay Co.), bentonite, talc, calcium carbonate, sodium carbonate, zeeklite, sericite, acid clay, quartzite, diatomaceous silica, pumice, zeolite, vermiculite, potassium chloride, urea, white carbon, ammonium sulfate, sodium sulfate, perlite, magnesium sulfate, attapulgite and the like; and examples of organic carriers including glucose, maltose, sucrose, lactose and the like.

Colorants can also be included in the formulations. Non-limiting examples of colorants include inorganic pigments, such as iron oxide, titanium oxide and Prussian Blue, and organic dyestuffs, such as alizarin dyestuffs, azo dye-stuffs and metal phthalocyanine dyestuffs, and trace nutrients such as salts of iron, manganese, boron, copper, cobalt, molybdenum and zinc.

The invention also provides methods for producing an encapsulated triazinyl sulfonylurea composition. In one embodiment, an encapsulated triazinyl sulfonylurea composition may be made by mixing (contacting) a triazinyl sulfonylurea with a silicone defoaming agent (e.g., a polydimethylsiloxane). In other embodiments, a method for producing an encapsulated triazinyl sulfonylurea composition includes a) mixing a triazinyl sulfonylurea with a silicone defoaming agent to form an encapsulated triazinyl sulfonylurea mixture; and b) drying the resulting mixture obtained to remove moisture.

In an additional embodiment, the triazinyl sulfonylurea is mixed with a silicone defoaming agent, such as a polydimethylsiloxane, and a silica to form an encapsulated triazinyl sulfonylurea mixture. In a further embodiment, a method for producing an encapsulated triazinyl sulfonylurea composition includes adding one or more adjuvants, or adding one or more active or inactive compounds, or both to the encapsulated triazinyl sulfonylurea mixture. In one exemplary embodiment, a method for producing an encapsulated triazinyl sulfonylurea composition includes a) mixing a triazinyl sulfonylurea with a silicone defoaming agent and a silica to form an encapsulated triazinyl sulfonylurea mixture, subsequently, adding one or more active or inactive compounds and one or more adjuvants to the encapsulated triazinyl sulfonylurea mixture to form a second mixture; and b) drying the resulting mixture obtained to remove moisture. The one or more active or inactive compounds may includes fluoroxypyr, or thifensulfuron-methyl, or both.

Compositions may be optionally dried such that the moisture content of the final composition is reduced, for example, to no more than about 10%. In particular embodiments, a composition is dried so that there is 5% or less by weight moisture in the composition (e.g., less than 3%, 2.5%, 2% or 1.5% by weight of the composition).

Compositions of the invention can be used in various formulations. Non-limiting examples include compositions in solutions, emulsions, suspensions, wettable powders, powders, dusts, pastes, soluble powders, granules, pellets, emulsifiable concentrate, oil spray, aerosol, natural and synthetic materials impregnated with active compound, and very fine capsules (e.g., in polymeric substances). Formulations can be applied in the form of ready mixes. Compositions can also be formulated individually and mixed upon use, i.e., combined in the form of tank mixes. The term "formulation" used herein indicates that the composition of the invention is formulated (e.g., mixed, added, dissolved, suspended, solubilized) with one or more other compositions, for example, for use in methods for weed control.

Invention compositions can be used for control of one or more weeds. Accordingly, the invention provides methods for selective control of a weed. In one embodiment, a method includes contacting a weed with a composition of the invention in an amount sufficient to inhibit growth of the weed.

Compositions of the invention can be used against one or more species of weeds. In the broadest sense, the term "weed"

refers to plants which grow in locations where they are not desired. In other words, a weed is a plant that in a given context, such as in the presence of a crop, is undesirable due to competition for soil, water, nutrients, sunlight, etc.

In methods of the invention, "control" and "controlling" includes any adverse modifying or detrimental effect on the natural plant (weed) survival, growth or development. Specific non-limiting examples include inhibiting, reducing, or preventing growth of all or any part of a weed (root, stem, stalk, leaf, flower, branch, etc.), weed germination, weed maturation, weed spreading, seed formation, flowering, or killing the weed. Broadleaf weeds are one particular example.

Weeds can be controlled using the compositions of the invention. The invention therefore provides methods for controlling weeds. In one embodiment, a method includes applying (contacting) a composition comprising an encapsulated triazinyl sulfonylurea to a weed, a crop or a plant habitat or area. Such methods are applicable to a plant including, but not limited to, one or more weeds described herein.

A weed can be controlled or suppressed in a pre-emergent or post-emergent growth stage at the time of applying (contact) of an invention composition or method. Accordingly, compositions of the invention can be applied before the weed has emerged (pre-emergence) or after the weed has emerged (post-emergence). They can be applied to all or a part of a weed, a crop or habitat area.

Examples of weed species against which the compositions and methods of the invention can be used include, but are not limited to, annual knawel, annual sowthistle, black mustard, bushy wallflower/treacle mustard, broadleaf dock, but buttercup, canada thistle, carolina geranium, catchweed bedstraw (cleavers), coast fiddleneck, coffee weed, common chickweed, common cocklebur, common groundsel, common lambsquarters, common purslane, common ragweed, common sunflower, common tarweed, corn chamomile, corn spurry, cow cockle, cress (mouse ear), curly dock, devilsclaw, false chamomile, field bindweed, field horsetail, filaree (Texas redstem), flixweed, giant ragweed, grape species, green smartweed, horseweed, hedge bindweed, hemp dogbane, henbit, jimsonweed, knotweed, kochia, ladysthumb, lanceleaf sage, london rocket, common mallow, little mallow, venice mallow, marestail, marshelder, miners lettuce, morningglory, mouseear chickweed, narrowleaf lambsquarters, nightflowering catchfly, nightshade species, pennsylvania smartweed, pepperweed species, pineappleweed, prickly lettuce, prostrate knotweed, prostrate pigweed, puncturevine, redmaids, redroot pigweed, russian thistle, scentless chamomile/mayweed, shepherd's purse, slimleaf lambsquarters, smallflower buttercup, smallseed falseflax. Stinking mayweed/dogfennel, swinecress, tansymustard, tarweed fiddleneck, tumble/Jim Hill mustard, velvetleaf, volunteer canola, volunteer flax, volunteer lentils, volunteer peas, volunteer sunflower, wild buckwheat, wild chamomile, wild garlic, wild mustard, wild radish, charlock, deadnettle red, fat hen, forget-me-not, fumitory, hemp-nettle common, poppy common, redshank, shepherds purse, cranesbill, bindweed black, knotgrass, marigold corn, orache, pansy, poppy, speedwell common field, speedwell wall, buttercup, docks, speedwell ivy-leaved, volunteer beans, and volunteer OSR.

Methods and uses of the compositions of the invention, however, need not be restricted to these weeds in any way. Accordingly, compositions and methods of the invention can be applied against other weeds in the same manner.

Desirable plants are generally referred to herein as "crop plants." The term "crop plants" as used herein, includes any edible or non-edible plant, including decorative, plant species with commercial value, which is planted and cultivated for commercial use. Thus, crop plants include floral and non-floral plants, trees, vegetable plants, turf, and ground cover. Non-limiting specific examples of crop plants include wheat (e.g., winter and spring wheat), barley (e.g., winter and spring barley), oat (e.g., winter and spring oats), triticale, cereals, rice, maize, sorghum, sugar cane, cotton, canola, turf, barley, pinapple, potato, sweet potato, sunflower, rye, corn, soybean, sugar beet, tobacco, safflower, tomato, alfalfa and cassava.

The term "plants" includes germinant seeds, emerging seedlings, and established vegetation, including roots and above-ground portions (e.g., leaves, stalks, flowers, fruits, branches, limbs, root, etc.). The term "turf" used herein refers to grasses which grow in areas in which they are desired, or purposely planned for and maintained, for example, a lawn. Turf also refers to a sod, where the surface layer of ground consists of a mat of grass and grass roots.

The application rate varies depending, for example, on the crop or the targeted weed environmental conditions, such as season, temperature, humidity, etc. In general, an application rate is from 0.01 kg/ha to 5.0 kg/ha, from 0.05 kg/ha to 2 kg/ha, or from 0.1 kg/ha to 1 kg/ha of the total active compounds. Particularly, an application rate is from 0.15 kg/ha to 0.25 kg/ha or from 0.3 kg/ha to 0.6 kg/ha of the total active compounds. In certain embodiments, an application rate of the encapsulated triazinyl sulfonylurea is from 0.001 kg/ha to 0.01 kg/ha, or from 0.004 kg/ha to 0.008 kg/ha of the active ingredient. An application rate of a non-encapsulated active or non active may be represented separately from 0.0005 kg/ha to 1.0 kg/ha. In one embodiment, an application rate of a non-encapsulated sulfonylurea (e.g. thifensulfuron-methyl) is from 0.0005 kg/ha to 0.1 kg/ha, or from 0.001 kg/ha to 0.05 kg/ha of the active ingredient. In one embodiment, an application rate of a non-encapsulated aryloxyalkanoic acid (e.g., fluoroxypyr-meptyl) is from 0.05 kg/ha to 0.5 kg/ha, or from 0.1 kg/ha to 0.2 kg/ha of active ingredient.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents and other references, citations cited herein are incorporated by reference in their entirety. In case of conflict, the specification, including definitions, will control.

As used herein, the singular forms "a", "and," and "the" include plural referents unless the context clearly indicates otherwise.

As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a percentage range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

As also used herein a series of range formats are used throughout this document. The use of a series of ranges includes combinations of the upper and lower ranges to provide a range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, and 150-171, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-171, and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

The following examples are merely illustrative of the present invention and they should not be considered as limiting the scope of the invention in any way, as these examples and other equivalents thereof will become apparent to those skilled in the art in light of the present disclosure and the accompanying claims. All percentages used in the application are percent weight by weight (w/w) unless otherwise noted.

Example 1

Preparation of Herbicidal Compositions Containing Tribenuron Methyl.

Tribenuron methyl and an antifoaming agent (e.g. Dow Corning 1400, PDMS, DC 200, 500 cSt, or Wacker AK 1000) were charged onto a ribbon blender with electronic load cells. Agitation was initiated and the mixture was blended for 20 minutes. A silica (e.g. Sipernat 35, Sipernat 350, or Sipernat D 17) and Stepsperse DF-500 ("first mix") were added to the mixture. Agitation was initiated and the mixture was blended until homogeneous. The mixture was further blended with Stepsperse® DF-200, Stepsperse® DF-500 ("second mix"), Sipernat 35, Metasperse 550S, sodium carbonate, lactose, Paragon® clay, Agnique ANS-3DNP-W, thifensulfron technical and fluoroxypyr technical until homogeneous.

The resulting material was then fed through a hammer mill to grind roughly to break up any lumps, and then fed through an air milling apparatus at a constant rate to produce particles essentially having an average size of less than 20 microns in diameter and a mean particle size of less than 5 microns. In one embodiment, 99% of the average particle size is less than 10 microns. In another embodiment, the mean particle is between 2.0 and 3.0 micros, or about 2.4 microns.

The homogenous mixture was transferred to a kneader and water was metered into the system to provide a consistent "dough-like" material that contains approximately 6-8% moisture. The mixture is extruded from a low-pressure extruder (less than 150 psi) which is equipped with a 1.25 mm dye. The "dough-like" material was fed gravimetrically into the extruder at a rate consistent with the auger speed to insure the pressure threshold of the dye was not exceeded. The feed rate was kept at 15-20 kg/hour at 12-56 rpm and the temperature was kept at below 50° C. during extrusion. The extruded material was allowed to break and free fall directly into a fluid bed dryer for drying where the moisture content was reduced to between 2-3%. The extrudates were flowed into a screening apparatus equipped with an 8 and 40 mesh US Sieve to separate oversized, good material, and fines.

The following herbicidal combination compositions in Table 1 were obtained according to the procedure described above.

TABLE 1

Herbicidal combination compositions.

| Ingredients | #1 | #2 | #3 | #4 | #6 | #7 | #8 | #9 | #10 | #11 | #12 | #13 |
|---|---|---|---|---|---|---|---|---|---|---|---|---|
| | | | | | | | Weight percentages | | | | | |
| Tribenuron methyl (96.36%) | 1.7 | 1.7 | 1.7 | 1.7 | 1.7 | 1.7 | 1.7 | 1.7 | 1.7 | 1.7 | 1.7 | 1.7 |
| DC antifoam 1400, (EPA. 180.910) | 0.6 | — | — | — | — | 0.6 | — | — | — | — | 0.6 | — |
| PDMS, DC 200, 500 cSt | — | 0.6 | — | — | 1.7 | — | 0.2 | — | 0.2 | — | — | — |
| Wacker AK 1000, (EPA: 180.960) | — | — | 0.6 | — | — | — | — | — | — | — | — | — |
| Sipernat 35, Pptd, hydrophilic | 0.3 | 0.3 | 0.3 | 0.3 | 0.3 | — | — | — | — | — | — | — |
| Sipernat 350, Pptd, hydrophilic | — | — | — | — | — | 0.3 | — | — | — | — | 0.3 | 0.3 |
| Sipernat D 17, (EPA 180.960) | — | — | — | — | — | — | 0.3 | 0.3 | 0.3 | — | — | — |
| Stepsperse DF 500 | 0.1 | 0.1 | 0.1 | 0.1 | 0.1 | 0.1 | 0.1 | 0.1 | 0.4 | 0.1 | 0.1 | 0.1 |
| Lactose, monohydrate | 3 | 3 | 3 | 3 | 8 | 3 | 3 | 0.6 | 3 | 3 | 3 | 3 |
| Fluroxypyr meptyl (98.5%) | 37 | 37 | 37 | 37 | 37 | 37 | 37 | 37 | 37 | 37 | 37 | 37 |
| Sipernat 35, Pptd, hydrophilic, silica | 9 | 9 | 9 | 9 | 9 | 9 | 9 | 9 | 9 | 9.3 | 9 | 9 |
| Thifensulfuron methyl (96.1%) | 4.7 | 4.7 | 4.7 | 4.7 | 4.7 | 4.7 | 4.7 | 4.7 | 4.7 | 4.7 | 4.7 | 4.7 |
| Stepsperse DF 500 | 9 | 9 | 9 | 9 | 9 | 9 | 9 | 9 | 9 | 9 | 9 | 9 |
| Stepsperse DF 200 | 3.5 | 3.5 | 3.5 | 3.5 | 3.5 | 3.5 | 3.5 | 3.5 | 3.5 | 3.5 | 3.5 | 3.5 |
| Metasperse 550S | 1 | 1 | 1 | 1 | 1 | 1 | 1 | 1 | 1 | 1 | 1 | 1 |
| Sodium carbonate, monohydrate | 1.4 | 1.4 | 1.4 | 1.4 | 1.4 | 1.4 | 1.4 | 1.4 | 1.4 | 1.4 | 1.4 | 1.4 |
| Lactose, monohydrate | 19.2 | 19.2 | 19.2 | 19.8 | 13.1 | 19.2 | 19.6 | 22.2 | 19.3 | 19.2 | 19.6 | 19.2 |
| Paragon Clay, soft air-floated, Kaolin | 8 | 8 | 8 | 8 | 8 | 8 | 8 | 8 | 8 | 8 | 8 | 8 |
| Agnique ANS 3DNPW | 0.5 | 0.5 | 0.5 | 0.5 | 0.5 | 0.5 | 0.5 | 0.5 | 0.5 | 0.5 | 0.5 | 0.5 |
| DC antifoam 1400, (EPA. 180.910) | — | — | — | — | — | — | — | — | — | 0.6 | — | 0.6 |

Physical Measurements

TABLE 1-continued

Herbicidal combination compositions.

| Ingredients | COMPOSITION EXAMPLES | | | | | | | | | | | |
|---|---|---|---|---|---|---|---|---|---|---|---|---|
| | #1 | #2 | #3 | #4 | #6 | #7 | #8 | #9 | #10 | #11 | #12 | #13 |
| | Weight percentages | | | | | | | | | | | |
| pH value | 9.63 | 9.6 | 9.8 | 9.67 | 9.8 | 9.79 | 9.8 | 9.7 | 9.7 | 9.9 | 8.3 | 10 |
| Moisture content (%) | 1.5 | 1.5 | 1.5 | 1.4 | 1.8 | 1.5 | 1.3 | 1.4 | 1.3 | 1.6 | 0.90 | 0.95 |

Example 2

Scale Up Preparation of Composition #7

To prepare a large batch of Formulation P7, 15.5 pounds of Tribenuron methyl and 6 pounds of Dow Corning 1400 were charged onto a ribbon blender with electronic load cells. Agitation was initiated and the mixture was blended for 20 minutes. 2 pounds of Sipernat 350, and 11 pounds of Stepsperse DF-500 ("first mix") were added to the mixture. Agitation was initiated and the mixture was blended until homogeneous. The resulting mixture has a pH value of above 9.0. The mixture was further blended with 35 pounds of Stepsperse® DF-200, 80 pounds of Stepsperse® DF-500 ("second mix"), 90 pounds of Sipernat 35, 10 pounds of Metasperse 550S, 14 pounds of sodium carbonate, 219.4 pounds of lactose, 85 pounds of Paragon® clay, 5 pounds of Agnique ANS-3DNP-W, 46 pounds of thifensulfron technical and 371.1 pounds of fluoroxypyr technical until homogeneous.

The resulting material was then fed through a hammer mill and an air milling apparatus, and further extruded and dried following the procedures described in Example 1.

Example 3

Stability Evaluation of Herbicidal Compositions Under Accelerated Storage Conditions The stability of the herbicidal compositions containing tribenuron methyl, fluoroxypyr meptyl and thifensulfuron methyl prepared in Example 1 was evaluated. Samples of the compositions were stored for 12 weeks at a constant temperature of 35° C. (which is the equivalent of storage at standard room temperature for a time of 2 years). The samples were analyzed for active ingredients content after the storage time period. Analyses were performed by reversed phase HPLC with a 240 nm UV detector (Luna C-18 (2) or equivalent, 150×4.6 mm). The percent recovery of the active ingredients were calculated using the equation shown below.

% Recovery=(Storage quantity/Initial quantity)×100

The results are shown in Table 2.

TABLE 2

Percentage of actives in herbicidal compositions containing tribenuron methyl, fluroxypyr meptyl and thifensulfuron methyl before and after 12 weeks of storage at 35° C.

| | Composition Examples | | | | | | | | | | | |
|---|---|---|---|---|---|---|---|---|---|---|---|---|
| | #1 | #2 | #3 | #4 | #6 | #7 | #8 | #9 | #10 | #11 | #12 | #13 |
| Percentage of active at time = 0 | | | | | | | | | | | | |
| Thifesulfuron methyl, % | 4.3 | 4.29 | 4.48 | 4.59 | 4.47 | 4.64 | 4.71 | 4.48 | 4.36 | 5.09 | 4.9 | 4.96 |
| Tribenuron methyl, % | 1.37 | 1.33 | 1.34 | 1.41 | 1.39 | 1.46 | 1.43 | 1.56 | 1.34 | 1.6 | 1.56 | 1.66 |
| Fluroxpyr meptyl, % | 36.84 | 36.84 | 36.69 | 36.69 | 36.49 | 37.03 | 36.84 | 35.72 | 36.12 | 37.54 | 37.51 | 37.84 |
| Percentage of active at end of week 12 | | | | | | | | | | | | |
| Thifesulfuron methyl, % | 4.42 | 4.49 | 4.79 | 4.86 | 4.71 | 4.81 | 4.73 | 4.45 | 4.53 | 4.79 | 4.63 | 4.69 |
| Tribenuron methyl, % | 1.34 | 1.4 | 1.44 | 1.4 | 1.27 | 1.35 | 1.34 | 1.46 | 1.29 | 1.17 | 0.39 | 1.44 |
| Fluroxpyr meptyl, % | 36.74 | 36.98 | 36.8 | 37.14 | 36.8 | 37.18 | 36.84 | 35.88 | 36.29 | 37.05 | 37.08 | 37.41 |

What is claimed is:

1. A stabilized composition, comprising a triazinyl sulfonylurea encapsulated with a coating of a silicone defoaming agent, wherein the composition contains no more than 3% by weight of moisture and has a pH of greater than 8.3.

2. The composition according to claim 1, wherein the triazinyl sulfonylurea is selected from the group consisting of tribenuron methyl, triflusulfuron methyl, metsulfuron methyl, iodosulfuron, cinosulfuron, prosulfuron, triasulfuron, tritosulfuron, chlorsulfuron, thifensulfuron methyl and ethametsulfuron-methyl.

3. The composition according to claim 1, wherein the triazinyl sulfonylurea is acid labile.

4. The composition according to claim 1, wherein the triazinyl sulfonylurea has a half life of more than 5 days.

5. The composition according to claim 1, wherein the triazinyl sulfonylurea is tribenuron methyl.

6. The composition according to claim 5, wherein the tribenuron methyl is present in an amount of from 0.05% to 20% by weight of the total weight of the composition.

7. The composition according to claim 5, wherein the tribenuron methyl is present in an amount of from 0.5% to 5% by weight of the total weight of the composition.

8. The composition according to claim 1, wherein the silicone defoaming agent is polydimethylsiloxane.

9. The composition according to claim 1, wherein the polydimethylsiloxane has a viscosity of from 10 cSt to 100,000 cSt.

10. The composition according to claim 8, wherein the polydimethylsiloxane is present in an amount of from 0.01% to 5% by weight of the total weight of the composition.

11. The composition according to claim 8, wherein the polydimethylsiloxane is present in an amount of from 0.05% to 1% by weight of the total weight of the composition.

12. The composition according to claim 1 further comprising a silica.

13. The composition according to claim 12, wherein the silica comprises a hydrophobic silica.

14. The composition according to claim 12, wherein the silica comprises a hydrophilic silica.

15. The composition according to claim 12, wherein the silica comprises a precipitated silica.

16. The composition according to claim 12, wherein the silica comprises a fumed silica.

17. The composition according to claim 12, wherein the silica is present in an amount of from 0.01% to 5% by weight of the total weight of the composition.

18. The composition according to claim 12, wherein the silica is present in an amount of from 0.05% to 1% by weight of the total weight of the composition.

19. The composition according to claim 1, wherein the weight ratio of the triazinyl sulfonylurea to the silicone defoaming agent is from 30 to 0.5.

20. The composition according to claim 12, wherein the weight ratio of the silicone defoaming agent to the silica is from 10 to 0.1.

21. The composition according to claim 1 further comprises one or more active compounds.

22. The composition according to claim 21, wherein the active compound is a herbicide.

23. The composition according to claim 22, wherein the herbicide comprises an aryloxyalkanoic acid.

24. The composition according to claim 23, wherein the aryloxyalkanoic acid is selected from the group consisting of fluoroxypyr meptyl, 4-CPA, 2,4-D, MCPA, Mecoprop, Mecoprop-P, 2,4,5-T, 3,4-DB, MCPB, 2,4,5-TB, cloprop, 4-CPP, dichorprop, dichlorprop-P, fenoprop, and Triclopyr.

25. The composition according to claim 23, wherein the aryloxyalkanoic acid is fluoroxypyr meptyl.

26. The composition according to claim 23, wherein the aryloxyalkanoic acid is present in an amount of from 10% to 75% by weight of the total weight of the composition.

27. The composition according to claim 23, wherein the aryloxyalkanoic acid is present in an amount of from 20% to 50% by weight of the total weight of the composition.

28. The composition according to claim 22, wherein the herbicide further comprises an additional triazinyl sulfonylurea.

29. The composition according to claim 28, wherein the additional triazinyl sulfonylurea is thifensulfuron methyl.

30. The composition according to claim 28, wherein the additional triazinyl sulfonylurea is present in an amount of from 1% to 10% by weight of the total weight of the composition.

31. The composition according to claim 1, wherein the composition has a pH between 9.0 to 10.0.

32. A method for selective control of a weed, comprising contacting the weed with a composition of any of claims 1-30, 31 in an amount effective inhibit growth of the weed.

33. The method according to claim 32, wherein the triazinyl sulfonylurea is selected from the group consisting of tribenuron methyl, metsulfuron methyl, ethametsulfuron methyl, cinosulfuron, prosulfuron, triasulfuron, tritosulfuron, chlorsulfuron, and ethametsulfuron-methyl.

34. The method according to claim 33, wherein the triazinyl sulfonylurea is tribenuron methyl.

35. The method according to any of claims 32-34, wherein the composition is applied at an application rate of from 0.001 kg/ha to 0.01 kg/ha of the triazinyl sulfonylurea.

36. The method according to claim 34, wherein the composition is applied at an application rate of from 0.004 kg/ha to 0.008 kg/ha of the tribenuron methyl.

37. The method according to any of claims 32-36, wherein the composition is applied as a pre-emergent treatment.

38. The method according to any of claims 32-36, wherein the composition is applied as a post-emergent treatment.

39. The method according to any of claims 32-38, wherein the weed is selected from the group consisting of annual knawel, annual sowthistle, black mustard, bushy wallflower/treacle mustard, broadleaf dock, but buttercup, canada thistle, carolina geranium, catchweed bedstraw (cleavers), coast fiddleneck, coffee weed, common chickweed, common cocklebur, common groundsel, common lambsquarters, common purslane, common ragweed, common sunflower, common tarweed, corn chamomile, corn spurry, cow cockle, cress (mouse ear), curly dock, devilsclaw, false chamomile, field bindweed, field horsetail, filaree (Texas redstem), flixweed, giant ragweed, grape species, green smartweed, horseweed, hedge bindweed, hemp dogbane, henbit, jimsonweed, knotweed, kochia, ladysthumb, lanceleaf sage, london rocket, common mallow, little mallow, venice mallow, marestail, marshelder, miners lettuce, morningglory, mouseear chickweed, narrowleaf lambsquarters, nightflowering catchfly, nightshade species, pennsylvania smartweed, pepperweed species, pineappleweed, prickly lettuce, prostrate knotweed, prostrate pigweed, puncturevine, redmaids, redroot pigweed, russian thistle, scentless chamomile/mayweed, shepherd's purse, slimleaf lambsquarters, smallflower buttercup, smallseed falseflax. Stinking mayweed/dogfennel, swinecress, tansymustard, tarweed fiddleneck, tumble/Jim Hill mustard, velvetleaf, volunteer canola, volunteer flax, volunteer lentils, volunteer peas, volunteer sunflower, wild buckwheat, wild chamomile, wild garlic, wild mustard, wild radish, charlock, deadnettle red, fat hen, forget-me-not, fumitory, hemp-nettle common, poppy common, redshank, shepherds purse, cranesbill, bindweed black, knotgrass, marigold corn, orache, pansy, poppy, speedwell common field, speedwell wall, buttercup, docks, speedwell ivy-leaved, volunteer beans, and volunteer OSR.

40. The composition according to claim 1, wherein the moisture content is less than 2.5%.

41. The method according to claim 32, wherein the moisture content is less than 2.5%.

42. The composition according to claim 1, wherein the moisture content is 0.90%, 0.95%, 1.3%, 1.4%, 1.5%, 1.6%, or 1.8%.

43. The method according to claim 32, wherein the moisture content is 0.90%, 0.95%, 1.3%, 1.4%, 1.5%, 1.6%, or 1.8%.

44. The composition according to claim 1, wherein the pH is about 9 to about 12.

45. The composition according to claim 1, wherein the pH is about 9 to about 10.

46. The method according to claim 32, wherein the pH is about 9 to about 12.

47. The method according to claim 32, wherein the pH is about 9 to about 10.

48. The composition according to claim 1, wherein the pH is 9.6, 9.7, 9.8, 9.9 or 10.

49. The method according to claim 32, wherein the pH is 9.6, 9.7, 9.8, 9.9 or 10.

50. A stabilized composition comprising i) tribenuron methyl encapsulated with a coating of polydimethylsiloxane and a hydrophilic silica, ii) fluoroxypyr meptyl, and iii) thifensulfuron methyl, wherein the composition contains no more than 3% by weight of moisture and has a off of greater than 8.3.

51. The composition according to claim 50, wherein the tribenuron methyl is present in an amount of from 1% to 2% by weight of the total weight of the composition.

52. The composition according to any of claims 50-51, wherein the fluoroxypyr meptyl is present in an amount of from 35% to 40% by weight of the total weight of the composition.

53. The composition according to any of claims 50-52, wherein the thifensulfuron methyl is present in an amount of from 3% to 6% by weight of the total weight of the composition.

54. The composition according to any of claims 50-53, wherein the polydimethylsiloxane is present in an amount of from 0.01% to 5% by weight of the total weight of the composition, and the silica is present in an amount of from 0.05% to 1% by weight of the total weight of the composition.

55. A liquid or solid formulation comprising the composition of any of claims 1-30, 31-54.

56. The composition according to claim 50, wherein the moisture content is less than 2.5%.

57. The composition according to claim 50, wherein the moisture content is 0.90%, 0.95%, 1.3%, 1.4%, 1.5%, 1.6%, or 1.8%.

58. The composition according to claim 50, wherein the pH is about 9 to about 12.

59. The composition according to claim 50, wherein the pH is about 9 to about 10.

60. The composition according to claim 50, wherein the pH is 9.6, 9.7, 9.8, 9.9 or 10.

61. A method for selective control of a weed, comprising contacting the weed with a composition of any of claims 50-54 in an amount effective inhibit growth of the weed.

62. The method according to claim 61, wherein the composition is applied at an application rate of from 0.004 kg/ha to 0.008 kg/ha of the tribenuron methyl.

63. The method according to claim 61, wherein the composition is applied as a pre-emergent treatment.

64. The method according to claim 61, wherein the composition is applied as a post-emergent treatment.

65. The method according to claim 61, wherein the weed is selected from the group consisting of annual knawel, annual sowthistle, black mustard, bushy wallflower/treacle mustard, broadleaf dock, but buttercup, canada thistle, carolina geranium, catchweed bedstraw (cleavers), coast fiddleneck, coffee weed, common chickweed, common cocklebur, common groundsel, common lambsquarters, common purslane, common ragweed, common sunflower, common tarweed, corn chamomile, corn spurry, cow cockle, cress (mouse ear), curly dock, devilsclaw, false chamomile, field bindweed, field horsetail, filaree (Texas redstem), flixweed, giant ragweed, grape species, green smartweed, horseweed, hedge bindweed, hemp dogbane, henbit, jimsonweed, knotweed, kochia, ladysthumb, lanceleaf sage, london rocket, common mallow, little mallow, venice mallow, marestail, marshelder, miners lettuce, morningglory, mouseear chickweed, narrowleaf lambsquarters, nightflowering catchfly, nightshade species, pennsylvania smartweed, pepperweed species, pineappleweed, prickly lettuce, prostrate knotweed, prostrate pigweed, puncturevine, redmaids, redroot pigweed, russian thistle, scentless chamomile/mayweed, shepherd's purse, slimleaf lambsquarters, smallflower buttercup, smallseed falseflax. Stinking mayweed/dogfennel, swinecress, tansymustard, tarweed fiddleneck, tumble/Jim Hill mustard, velvetleaf, volunteer canola, volunteer flax, volunteer lentils, volunteer peas, volunteer sunflower, wild buckwheat, wild chamomile, wild garlic, wild mustard, wild radish, charlock, deadnettle red, fat hen, forget-me-not, fumitory, hemp-nettle common, poppy common, redshank, shepherds purse, cranesbill, bindweed black, knotgrass, marigold corn, orache, pansy, poppy, speedwell common field, speedwell wall, buttercup, docks, speedwell ivy-leaved, volunteer beans, and volunteer OSR.

66. The method according to claim 61, wherein the moisture content is less than 2.5%.

67. The method according to claim 61, wherein the moisture content is 0.90%, 0.95%, 1.3%, 1.4%, 1.5%, 1.6%, or 1.8%.

68. The method according to claim 61, wherein the pH is about 9 to about 12.

69. The method according to claim 61, wherein the pH is about 9 to about 10.

70. The method according to claim 61, wherein the pH is 9.6, 9.7, 9.8, 9.9 or 10.

71. A method for producing a stabilized encapsulated triazinyl sulfonylurea composition, comprising: a) mixing a triazinyl sulfonylurea with a silicone defoaming agent to form an encapsulated triazinyl sulfonylurea mixture; and b) drying the resulting mixture obtained from step a) to remove moisture, thereby forming the encapsulated triazinyl sulfonylurea composition, wherein the composition contains no more than 3% by weight of moisture and has a pH of greater than 8.3.

72. The method of claim 71, further comprises adding one or more active or inactive compounds to the encapsulated triazinyl sulfonylurea mixture of step a) to form a second mixture.

73. The method of claim 71, further comprises adding one or more adjuvant to the encapsulated triazinyl sulfonylurea mixture of step a) to form a second mixture.

74. The method of claim 71, wherein step a) further comprises mixing the triazinyl sulfonylurea with a silica.

75. The method of claim 74, wherein the silicone defoaming agent comprises a polydimethylsiloxane.

76. The method of claim 72, wherein the one or more active or inactive compounds comprises fluoroxypyr.

77. The method of claim 72, wherein the one or more active or inactive compounds comprise thifensulfuron-methyl.

78. The method according to claim 71, wherein the moisture content is less than 2.5%.

79. The method according to claim 71, wherein the moisture content is 0.90%, 0.95%, 1.3%, 1.4%, 1.5%, 1.6%, or 1.8%.

80. The method according to claim 71, wherein the pH is about 9 to about 12.

81. The method according to claim 71, wherein the pH is about 9 to about 10.

82. The method according to claim 71, wherein the pH is 9.6, 9.7, 9.8, 9.9 or 10.

* * * * *